United States Patent
Herr et al.

(10) Patent No.: US 11,026,815 B2
(45) Date of Patent: *Jun. 8, 2021

(54) CONTROLLING POWER IN A PROSTHESIS OR ORTHOSIS BASED ON PREDICTED WALKING SPEED OR SURROGATE FOR SAME

(71) Applicant: BIONX MEDICAL TECHNOLOGIES, INC., Bedford, MA (US)

(72) Inventors: Hugh Miller Herr, Somerville, MA (US); Richard J. Casler, Jr., Lowell, MA (US); Zhixiu Han, Acton, MA (US); Christopher Eric Barnhart, Carlisle, MA (US); Gary Girzon, Sudbury, MA (US)

(73) Assignee: OTTO BOCK HEALTHCARE LP, Austin, TX (US)

( * ) Notice: Subject to any disclaimer, the term of this patent is extended or adjusted under 35 U.S.C. 154(b) by 422 days.

This patent is subject to a terminal disclaimer.

(21) Appl. No.: 15/377,360

(22) Filed: Dec. 13, 2016

(65) Prior Publication Data

US 2017/0143516 A1    May 25, 2017

Related U.S. Application Data

(63) Continuation of application No. 14/136,344, filed on Dec. 20, 2013, now Pat. No. 9,693,883, which is a
(Continued)

(51) Int. Cl.
*A61F 2/70* (2006.01)
*A61F 2/66* (2006.01)
(Continued)

(52) U.S. Cl.
CPC .............. *A61F 2/70* (2013.01); *A61F 2/6607* (2013.01); *A61F 2/68* (2013.01); *A61F 5/0127* (2013.01);
(Continued)

(58) Field of Classification Search
None
See application file for complete search history.

(56) References Cited

U.S. PATENT DOCUMENTS

| 5,343,397 A | * | 8/1994 | Yoshino | ............... B62D 57/032 |
| | | | | 180/8.1 |
| 9,693,883 B2 | * | 7/2017 | Herr | ...................... A61F 2/6607 |

(Continued)

*Primary Examiner* — David H Willse
(74) *Attorney, Agent, or Firm* — Kacvinsky Daisak Bluni PLLC

(57) ABSTRACT

In some embodiments of a prosthetic or orthotic ankle/foot, a prediction is made of what the walking speed will be during an upcoming step. When the predicted walking speed is slow, the characteristics of the apparatus are then modified so that less net-work that is performed during that step (as compared to when the predicted walking speed is fast). This may be implemented using one sensor from which the walking speed can be predicted, and a second sensor from which ankle torque can be determined. A controller receives inputs from those sensors, and controls a motor's torque so that the torque for slow walking speeds is lower than the torque for fast walking speeds. A controller determines a desired torque based on the output, and controls the motor's torque based on the determined desired torque.

19 Claims, 13 Drawing Sheets

Related U.S. Application Data continuation of application No. 13/079,564, filed on Apr. 4, 2011, now abandoned.

(60) Provisional application No. 61/432,083, filed on Jan. 12, 2011, provisional application No. 61/422,873, filed on Dec. 14, 2010, provisional application No. 61/320,991, filed on Apr. 5, 2010.

(51) Int. Cl.
  *A61F 2/76* (2006.01)
  *A61F 5/01* (2006.01)
  *A61F 2/68* (2006.01)
  *A61F 2/50* (2006.01)
  *A61F 2/60* (2006.01)
  *A61F 2/74* (2006.01)

(52) U.S. Cl.
  CPC . *A61F 2002/5003* (2013.01); *A61F 2002/503* (2013.01); *A61F 2002/5007* (2013.01); *A61F 2002/5018* (2013.01); *A61F 2002/5033* (2013.01); *A61F 2002/607* (2013.01); *A61F 2002/6685* (2013.01); *A61F 2002/701* (2013.01); *A61F 2002/704* (2013.01); *A61F 2002/745* (2013.01); *A61F 2002/763* (2013.01); *A61F 2002/7625* (2013.01); *A61F 2002/7635* (2013.01); *A61F 2002/7645* (2013.01); *A61F 2002/7695* (2013.01); *A61F 2005/0155* (2013.01)

(56) References Cited

U.S. PATENT DOCUMENTS

| | | | |
|---|---|---|---|
| 2008/0188907 A1* | 8/2008 | Aguirre-Ollinger | A61H 1/0237 607/48 |
| 2009/0265018 A1* | 10/2009 | Goldfarb | A61F 2/60 623/40 |

* cited by examiner

CONTROLLING POWER IN A PROSTHESIS OR ORTHOSIS BASED ON PREDICTED WALKING SPEED OR SURROGATE FOR SAME

CROSS REFERENCE TO RELATED APPLICATIONS

This Application is a continuation of U.S. patent application Ser. No. 14/136,344, filed Dec. 20, 2013 (now U.S. Pat. No. 9,693,883), which is a continuation of U.S. patent application Ser. No. 13/079,564, filed Apr. 4, 2011 (now abandoned), which claims the benefit of U.S. Provisional Applications 61/320,991 filed Apr. 5, 2010, 61/422,873 filed Dec. 14, 2010, and 61/432,083 filed Jan. 12, 2011, each of which is incorporated herein by reference.

BACKGROUND

US published patent applications 2010/0174384 ("the '384 application") and 2006/0249315, each of which is incorporated herein by reference, describe that the gait cycle for walking can be divided into five phases: controlled plantarflexion, controlled dorsiflexion (CD), powered plantarflexion (PP), early swing, and late swing, as depicted in FIG. 1.

The '384 application also discloses a number of embodiments of lower-extremity prosthetic and orthotic systems in which the reflex torque generation during PP is achieved via non-linear, positive feedback between the series elastic element (SEE) motor torque and ankle torque. More specifically, the reflex action involves behaving like a non-linear spring during CD and like a torque source during PP. This reflex action can be implemented by driving the motor using the following equation:

$$\text{Motor Torque} = pff \times (\text{normalized\_Torque})^n \qquad \text{Eq. 1}$$

Where, pff is the power control gain tuned for high walking speed; normalized_Torque is the ankle torque, FA, normalized by a torque, To, (strongly related to users' weight); n is the power exponent, typically in the range of between 3 and 5 for level-ground walking. Note that pff has units of N-m, and the value of pff controls the magnitude of the level of the torque reflex during fast walking. Once the desired motor torque is determined, the drive current can be computed based on the equation Motor Current=Motor Torque/kt, where kt is the motor torque constant. While using Equation 1 does provide good results, the results provided by the control approach described below are significantly better.

SUMMARY OF THE INVENTION

One aspect of the invention is directed to an ankle-foot prosthesis or orthosis apparatus. The apparatus includes a shank member and a foot member that is operatively configured with respect to the shank member so as to supporting walking and permit the foot member to plantarflex and dorsiflex with respect to the shank member. A motor is configured to plantarflex the foot member with respect to the shank member, and a series elastic element is connected between at least one of (a) the motor and the shank member and (b) the motor and the foot member. There is at least one first sensor having an output from which a walking speed of an upcoming step can be predicted, and at least one second sensor having an output from which ankle torque can be determined. The apparatus also includes a controller configured to control the motor's torque, based on the output of the at least one first sensor and the at least one second sensor, so that the motor's torque for slow walking speeds is lower than the motor's torque for fast walking speeds.

Another aspect of the invention is directed to a method of modifying characteristics of an ankle-foot prosthesis or orthosis apparatus. The method includes the steps of predicting what a walking speed will be during an upcoming step and modifying a characteristic of the apparatus during the upcoming step in situations when the predicted walking speed is slow. The modification of the characteristic results in a reduction in net non-conservative work that is performed during the upcoming step as compared to the net non-conservative work that is performed when the predicted walking speed is fast.

Another aspect of the invention is directed to an apparatus that includes a proximal member and a distal member that is operatively connected with respect to the proximal member by a joint so that an angle between the distal member and the proximal member can vary. A motor is configured to vary the angle between the distal member and the proximal member, and a series elastic element is connected between at least one of (a) the motor and the proximal member and (b) the motor and the distal member. There is a least one first sensor having an output from which a walking speed of an upcoming step can be predicted, and at least one second sensor having an output from which a joint torque can be determined. The apparatus also includes a controller configured to control the motor's torque, based on the output of the at least one first sensor and the at least one second sensor, so that the motor's torque for slow walking speeds is lower than the motor's torque for fast walking speeds.

Another aspect of the invention is directed to an ankle-foot prosthesis or orthosis apparatus that includes a shank member and a foot member that is operatively configured with respect to the shank member so as to supporting walking and permit the foot member to plantarflex and dorsiflex with respect to the shank member. A motor is configured to plantarflex the foot member with respect to the shank member, and a series elastic element is connected between at least one of (a) the motor and the shank member and (b) the motor and the foot member. The apparatus also includes at least one sensor having an output from which a deflection of the series elastic element can be determined, and a controller configured to determine a desired torque based on the output, and to control the motor's torque based on the determined desired torque.

Another aspect of the invention is directed to a method of controlling an ankle-foot prosthesis or orthosis having a foot member and shank member, with a motor configured to plantarflex the foot member with respect to the shank member and a series elastic element in series with the motor. The method includes the steps of sensing a position of the motor, determining a deflection of the series elastic element while the motor is at the position sensed in the sensing step, and controlling the motor's torque based on the motor position sensed in the sensing step and the deflection determined in the determining step.

Another aspect of the invention is directed to an apparatus that includes a proximal member, a distal member that is operatively configured with respect to the proximal member so that an angle between the distal member and the proximal member can vary, and a motor configured to vary the angle between the distal member and the proximal member. A series elastic element is connected between at least one of (a) the motor and the proximal member and (b) the motor and the distal member, and at least one sensor having an output from which a deflection of the series elastic element can be determined. The apparatus also includes a controller configured to determine a desired torque based on the output, and to control the motor's torque based on the determined desired torque.

DESCRIPTION OF THE PREFERRED EMBODIMENTS

Figure 1:
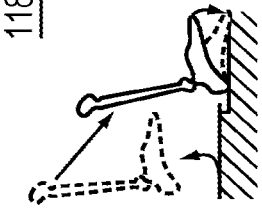
FIG. 1 is a schematic illustration of the phases of a user's gait cycle when walking on level ground.
Figure 2A:
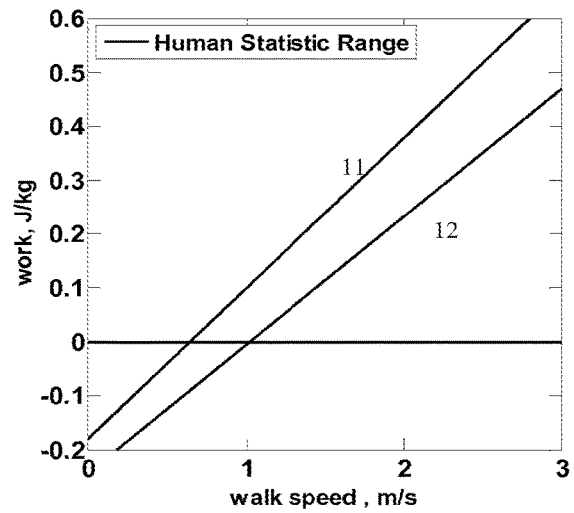
FIG. 2A depicts the statistic range of net non-conservative work vs. walking speed for healthy human ankles.
Figure 2B:
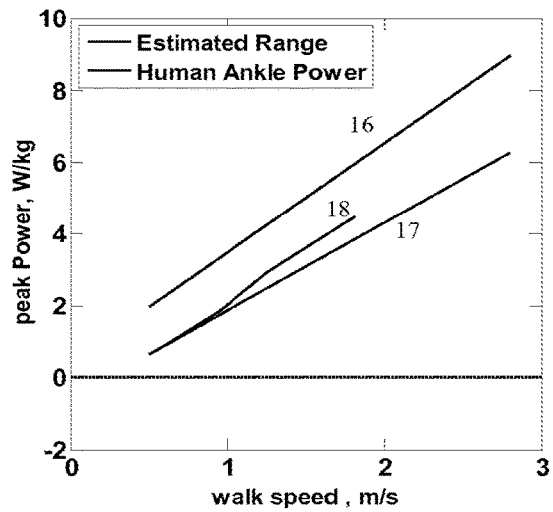
FIG. 2B depicts the statistic range of peak-power vs. walking speed for healthy human ankles.

In healthy humans, the ankle-foot normally creates the positive net-work and peak-power on each stride that the body needs to achieve ordinary walk with metabolic efficiency. The net-work and peak-power in the ankle during the stance of gait is highly related to walking speed. FIGS. 2A and 2B depict this relationship. More specifically, FIG. 2A shows the statistic range (+1 sigma bounds) of net non-conservative work vs. walking speed, which lies between the lines 11, 12. FIG. 2B shows the estimated statistic ranges (+1 sigma bounds) of the peak-power vs. walking speed as lines 16, 17. FIG. 2B also shows the mean value of peak-power vs. walking speed (as measured in a study) as line 18, which lies between lines 16 and 17.

Figure 2C:
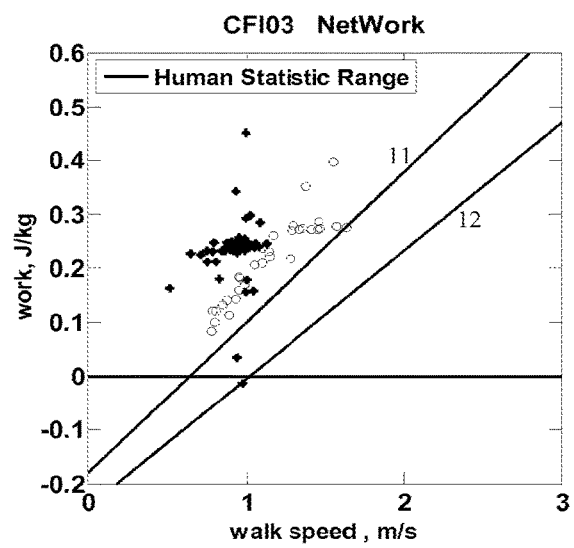
FIG. 2C shows the net non-conservative work vs. walking speed when two different equations are used to control a motor.
Figure 2D:
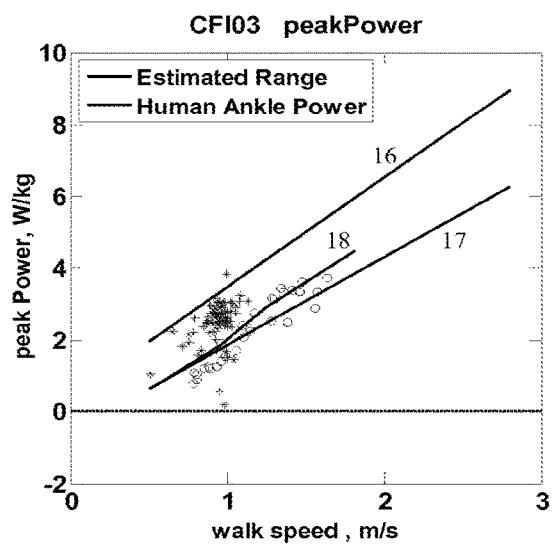
FIG. 2D shows peak-power vs. walking speed when two different equations are used to control a motor.
Figure 10:
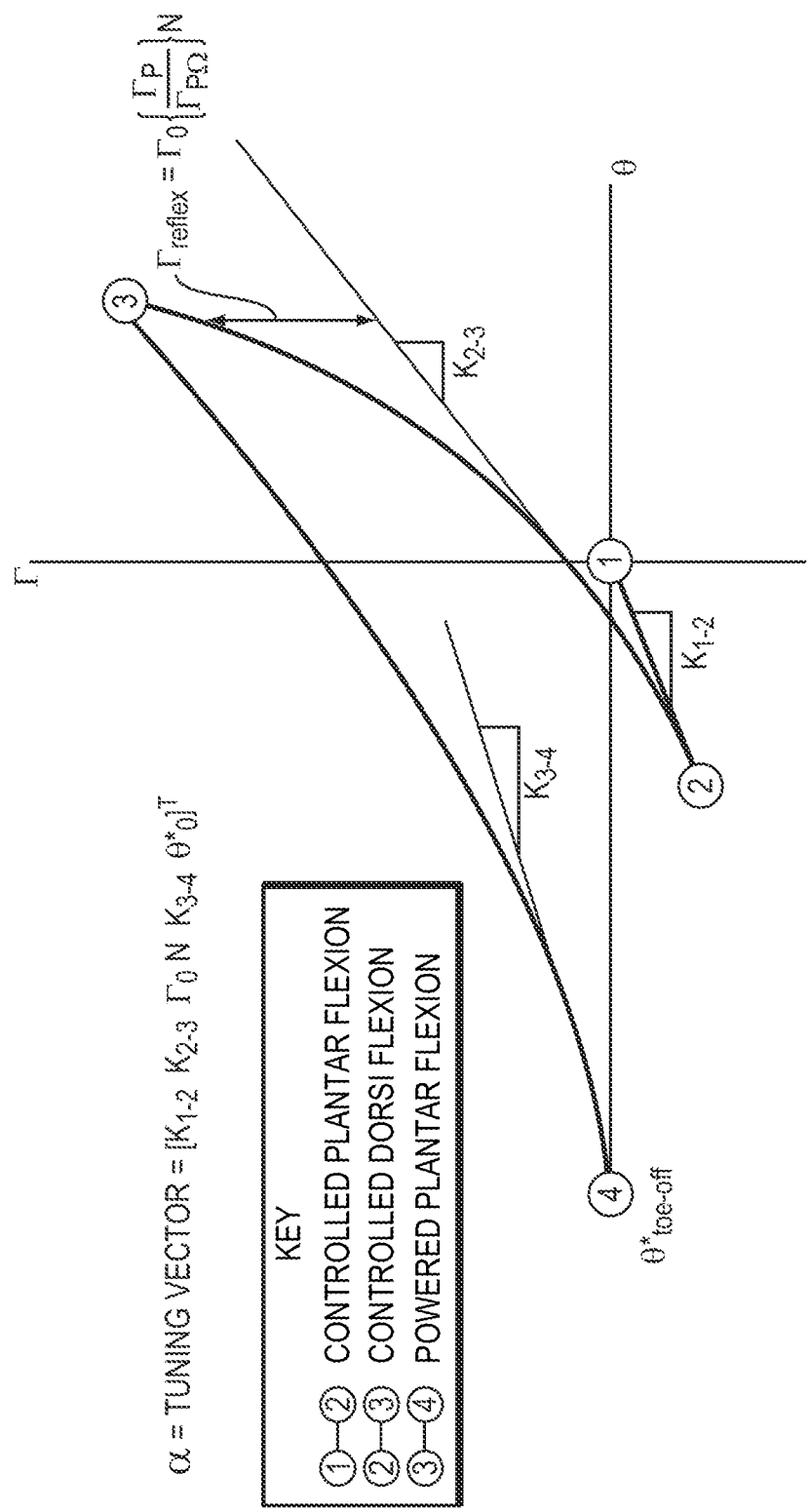
FIG. 10 is a Γ–Θ plot for the stance-phase torque-angle response of an intact ankle.

The data points depicted by stars in FIG. 2C shows the net non-conservative work vs. walking speed when Equation 1 above is used to control the motor current. Note that net non-conservative work can be determined by calculating the loop area, over one cycle of ankle-torque vs. ankle angle (e.g., as seen in FIG. 10, starting at point 1, passing through points, 2, 3, and 4 in sequence, and returning to point 1. It can be seen that the net non-conservative work is higher than the statistic range bounded by lines 11, 12 for intact ankles, and the deviation from that range is larger at slower walking speeds than it is at faster walking speeds. Similarly, the data points depicted by stars in FIG. 2D show the peak power vs. walking speed when Equation 1 above is used to control the motor current. It can be seen that the peak power is higher than the mean value line 18 for intact ankles. The net work is also higher, and is wasted, causing extra heat and reduction in battery life.

To more closely mimic the human ankle-foot biomechanics for ordinary walk across a wide range of walking speeds, the embodiments disclosed in the '384 application may be modified by using the power control approach described herein so as to deliver net-work and peak-power on each stride that more closely matches the statistic ranges bounded by the lines 11, 12 in FIG. 2A, and the mean line 18 in FIG. 2B, In this approach, a prediction of the walking speed for the upcoming step is made, and that predicted walking speed is used to set the ankle control parameters (including setting of the power control gain) for the upcoming step.

Figure 3A:
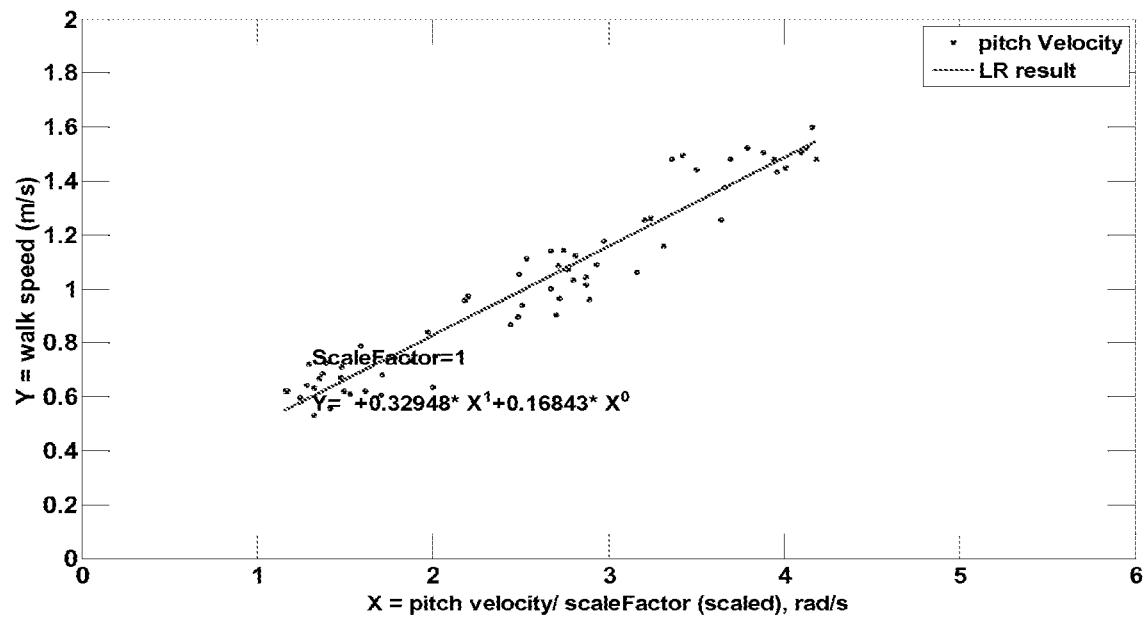
FIG. 3A depicts the relationship between walking speed of the upcoming step and the shank angular rate.

One way to predict the walking speed of the upcoming step is based on the shank (pitch) angular rate $\omega_x$ based on the relationship depicted in FIG. 3A. These two velocities are highly linearly correlated such that the peak angular rate in stance phase serves as an excellent prediction of the walk speed of the up coming step. The correlation between walking speed and the shank angular rate is present at various times during the stance and swing phase, but it is preferable to minimize the latency between the walking speed estimate and when it will be applied. One way to accomplish this is to sample the shank angular rate at the very start of controlled dorsiflexion (i.e., at foot-flat), immediately before the reflex begins. This reduced latency ensures that a reflex is not applied in certain situations, such as when the user is stopping. If, on the other hand, a stale walking-speed prediction were used, (e.g., by estimated walking speed from the shank angular rate at the prior toe-off), the estimate might be invalid (e.g., in situations where the user decides to stop suddenly).

Figure 3B:
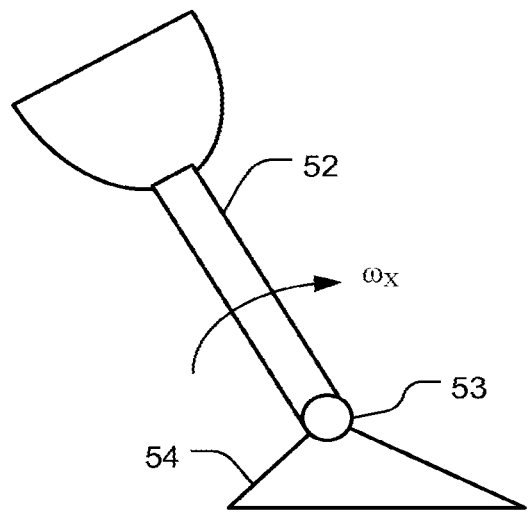
FIG. 3B depicts what shank angular rate is used in FIG. 3A.

The shank angular rate may be measured by any suitable means, such as an inertial measurement unit (IMU) or an angular rate sensor (ARS). The IMU or ARS may be placed onto the top part of the prosthesis or orthosis that is rigidly connected to a socket such that shank angular rate, as depicted in FIG. 3B, can be measured. In alternative embodiments, it could be mounted on the foot structure. An example of a suitable angular rate sensor is the Invensense IDG-300. In one preferred embodiment, the IMU can be made from three orthogonally-aligned angular rate sensors such as the Analog Devices ADXRS610, and three orthogonally-aligned accelerometers such as the Freescale MMA7360L.

An advantage of using the angular rate sensing technique is that it provides an instantaneous measure of angular rate just prior to invoking the reflex control. More specifically, the maximum angular rate in the stance phase can be calculated and employed to adjust the reflex torque response during the controlled dorsiflexion and powered plantar flexion phases of a step. This reflex is largely responsible for generating the net-work and peak-power that meet human ankle-foot needs for ordinary walking.

Figure 4A:
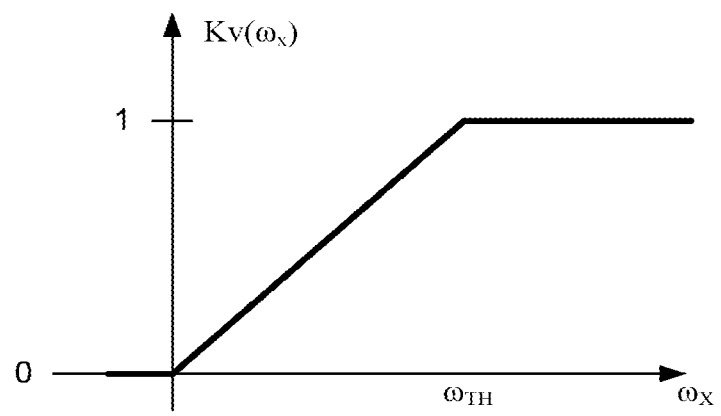
FIG. 4A depicts one suitable gain function for use in controlling the motor.

The reflex torque generation is achieved via non-linear, positive feedback between the series elastic element (SEE)

motor torque and ankle torque by controlling the motor using the following equation:

$$\text{Motor Torque} = Kv(\omega_x) \times pff \times (\text{normalized\_Torque}) \qquad \text{Eq. 2}$$

where $Kv(\omega_x)$ is a power control gain function related to the maximum angular rate, an example of which is depicted in FIG. 4A; pff is the power control gain tuned for high walking speed; normalized_Torque is the ankle torque, $\Gamma_A$, normalized by a torque, $\Gamma_0$, (strongly related to users' weight); and n is the power exponent, typically in the range of between 3 and 5 for level-ground walking. This is similar to Equation 1 above, except that the right side of the equation is multiplied by a gain function $Kv(\omega_x)$ that is selected to reduce the motor torque for lower angular velocities, which correspond to slower walking speeds. Note that the companion equation for converting a desired motor torque to a drive current for the motor remains the same for all embodiments described herein (i.e., Motor Current=Motor Torque/kt, where kt is the motor torque constant).

One suitable gain function $Kv(\omega_x)$ is depicted in FIG. 4A, which starts at 0 when the angular rate is zero, and increases linearly to 1 at an angular rate W that corresponds to a fast walking speed. Above that threshold angular rate $\omega_{TH}$, the gain function $Kv(\omega_x)$ remains at 1. A suitable setting for the threshold $\omega_{TH}$ is an angular rate that corresponds to a fast walking speed (e.g., an angular rate that corresponds to a walking speed of between 1.5 and 1.75 meters per second). In some embodiments, the threshold point may be settable by a prosthetist, preferably constrained to some legal range (e.g., to an angular rate that corresponds to a walking speed of between 1.25 and 2 meters per second). In other embodiments, provisions for adjusting the $\omega_{TH}$ set point within a legal range may even be made available to the end user.

The result of multiplying the right side of Equation 2 by $Kv(\omega_x)$ is that the motor will be driven by lower currents for slower walk speeds. That will result in less torque at slower walk speeds (as compared to when Equation 1 is used). When this approach is used to control a prosthetic or orthotic ankle, during the flat-foot portion of the gait the torque will initially be zero. The ankle torque $\Gamma_A$ will start to increase at the end of the controlled dorsiflexion phase. In response to the rising $\Gamma_A$, the controller will drive the motor based on Equation 2, which will increase the torque further in a positive feedback reflex response. This positive feedback continues until prior to toe-off as the lower leg begins to lift the foot off the ground. At this point the positive feedback is diminishing, so the torque starts to drops off. The positive feedback is quenched at toe-off because at that point there is nothing to push against, which makes the torque fall off rapidly. In addition, the state machine that controls the application of the reflex also transitions to the swing phase where position control is used. Note that operation of the state machine is described in the '384 application, which is incorporated herein by reference.

The speed based power control method of Equation 2 has been implemented and tested on an iWalk™ Powerfoot™ BiOM™ prosthetic ankle/foot. When Equation 2 was used to control the motor, the net non-conservative work vs. walking speed is depicted by the circle data points in FIG. 2C. A comparison between the circle data points and the star data points (discussed above) in FIG. 2C reveals that the net non-conservative work is closer to the statistic range bounded by lines 11, 12 when Equation 2 is used. Similarly, the circle data points in FIG. 2D show the peak power vs. walking speed when Equation 2 above is used to control the motor current. It can be seen that the peak power when Equation 2 is used is much closer to the mean value line 18 than when Equation is used (indicated by the star data points in FIG. 2D). This experiment result was obtained from a patient with weight of 240 lb and shank length of 53 cm. The walk speed was measured using IMU systems, and ranged from 0.8 m/s to 1.5 m/s. The system provided smooth transitions of power when users randomly changed their walking velocities.

Figure 4B:
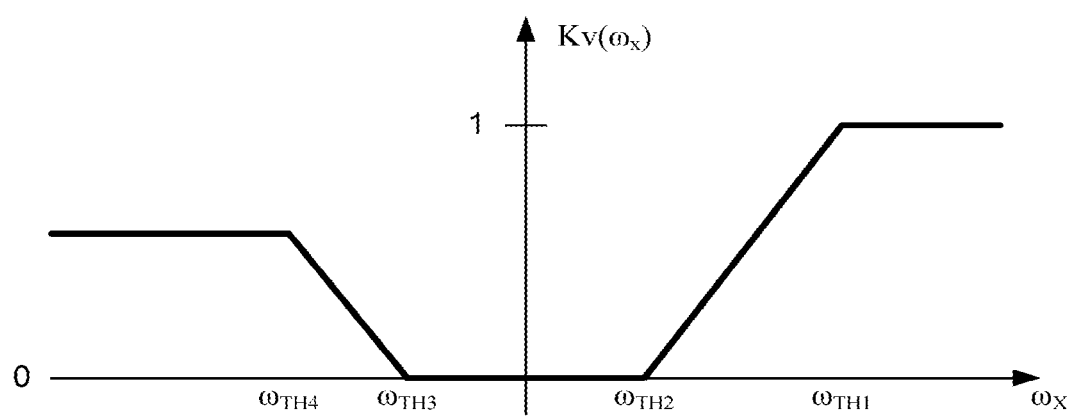
FIG. 4B depicts another suitable gain function.

In alternative embodiments, gain functions with other shapes may be used instead of the ramp depicted in FIG. 4A. Preferably, all such functions start at 0 when $\omega_x=0$, end at 1, and are monotonically increasing. Examples of suitable shapes for the gain function include shapes that resemble (a) the first quadrant of a sine curve; or (b) the third and fourth quadrants of a cosine curve (scaled and offset so as to start at 0 and end at 1). Other transition shapes, including smooth shapes and shapes with abrupt changes, may also be used. For example, the curve depicted in FIG. 4B would operate to keep the power low for low walking speeds (which would be suitable in certain situations like a classroom), and increase it only if the speed goes over a threshold $\omega_{TH2}$. Optionally, the gain function may also be operative for negative velocities to control the reflex response when walking or running backward. For this reason, negative velocities are included in FIG. 4B. If desired, the maximum gain for negative velocities may be lower than 1, so as to provide a smaller power boost when walking backwards In some embodiments, the gain function could also be made to be a function of velocity when side-stepping or hopping sideways.

In some embodiments, a user interface may be provided to give the prosthetist control over the value of n in Equation 2, preferably constrained within some legal range (e.g., between 2 and 7). Set points of between 3 and 5 have been found to be preferable. Since normalized_Torque is $\Gamma_A$ normalized by $\Gamma_0$, when n is high (e.g., around 5), the current will not rise until $\Gamma_A$ gets closer to $\Gamma_0$. This delays (in time) the onset of the positive feedback. Conversely, when n is lower (e.g., around 3), the current will start to increase before $\Gamma_A$ gets too close to $\Gamma_0$. This advances (in time) the onset of the positive feedback. When the system is configured to give the prosthetist control over n, n can be adjusted (e.g., based on verbal feedback from the end user) to maximize the user's comfort. In other embodiments, a user interface may be provided to give the end user control over n (within a legal range).

In alternative embodiments, the reflex torque generation equation may be modified to be as follows:

$$\text{Motor Torque} = Kv(\omega_x) \times pff \times (\text{normalized\_Torque})^{n f(\omega_x)} \qquad \text{Eq. 3}$$

Equation 3 is very similar to Equation 2, except that in Equation 3, the exponent n of the normalized_Torque is multiplied by a function of the angular rate $\omega_x$. The function $f(\omega_x)$ is preferably selected so that the resulting exponent is larger at higher angular velocities than it is at lower angular velocities. This would operate to advance the onset of reflex (in time) when the user is walking faster, with respect to the timing when the user is walking slower.

Note that in the embodiments described above, the system does not explicitly make a prediction of the walking speed for the upcoming step. Instead, the system relies on the angular rate $\omega_x$ of the shank (which, as described above, is correlated to the predicted walking speed). In this case, the angular rate $\omega_x$ of the shank serves as a surrogate for the walking speed. In alternative embodiments, instead of relying on the angular rate $\omega_x$ of the shank, other parameters may be used to predict the walking speed. The ankle power would then be adjusted accordingly based on the predicted walking speed based on these alternative sensors. For example, the angular rate of the leg section above the knee, or the knee linear moving velocity in stance phase may be used to predict the walking speed of the upcoming step. The Cartesian trajectory of the ankle or knee, tracked using an IMU, could also be used to predict the walking speed of the upcoming step.

In other embodiments, the equations may implemented so as to explicitly compute the estimated walking speed as an intermediate result, and then adjust the various parameters based on that intermediate result to control the power and net non-conservative work (e.g., by replacing $Kv(\omega_x)$ with Kv(speed) in Equation 2).

Preferably, the system includes special-event handing to modify the power level when it determines that a special walking environment exists. For example, the power may be increased for upstairs/up-ramp walking, even though the walk speed is low. Or the power may be decreased for down stairs or down ramp walking even though the walk speed is high. Note that the ankle trajectory or knee trajectory (determined, for example, using an IMU) may be used as a discriminator to determine if a special walking environment exists, so that the characteristics of the ankle (including the reflex) can be adjusted for the special walking environment.

The system described above provides users improved net-work and peak-power to achieve normal biomechanics for ordinary walking across a range of walking speeds. The system also uses reduced motor current at low walking speeds, which is the case for the majority of walking in most people's routines. This may help keep the motor temperature low, save energy, and reduce the frequency of recharging batteries and the need to carry spare batteries. Lower currents also reduce the stress and fatigue on the drive transmission, including the series-spring, and can increase the design life of various components in the device.

The embodiments described above rely on the ankle torque $\Gamma_A$ as an input to the equations that ultimately control the motor current during controlled dorsiflexion and powered plantar flexion. This ankle torque $\Gamma_A$ may be determined by a number of approaches. One such approach, which is described in the '384 application, is to actively measure the ankle torque $\Gamma_A$ using, for example, strain gauges arranged in a Wheatstone bridge configuration to measure the torque applied by the socket attachment at the top of the ankle prosthesis.

Figure 5A:
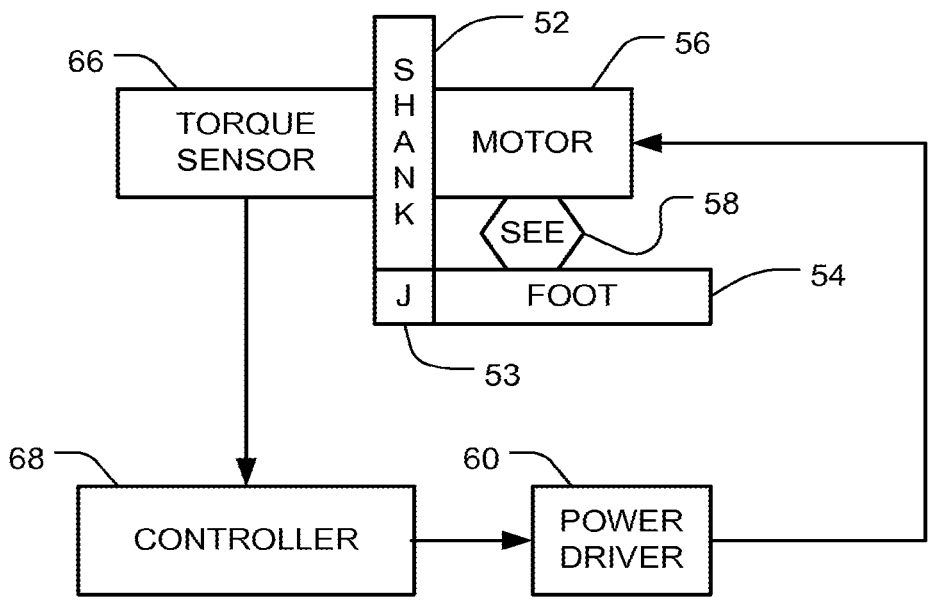
FIG. 5A is a block diagram of an embodiment that relies on torque sensing.

FIG. 5A is a system block diagram for this embodiment. The prosthetic or orthotic ankle/foot includes a shank member 52 and a foot member 54 operatively connected to permit plantarflexion and dorsiflexion, e.g., by a joint 53. A motor 56 is affixed to the shank member 52, and a series elastic element 58 sits between the shank member 52 and the foot member 54, so that it will be in series with the motor, as explained in U.S. Pat. No. 5,650,704, which is incorporated herein by reference. Driving the motor in one direction or the other will plantarflex or dorsiflex the foot member 54 with respect to shank member 52. In alternative embodiments (not shown) the positions of the motor 56 and the series elastic element 58 could be swapped, in which case the motor would be mounted to the foot member 54.

A torque sensor 66 measures the ankle torque $\Gamma_A$ and send an output that represents that torque to the controller 68. The controller 68 is programmed to control the motor 56 by implementing Equation 2 In alternative embodiments, analog circuitry configured to implement Equation 2 may be used in place of the controller 68. The power driver 60 contains the drive circuitry needed to convert the low level signals from the controller 68 into the high power signals needed to drive the motor 56.

Figure 5B:
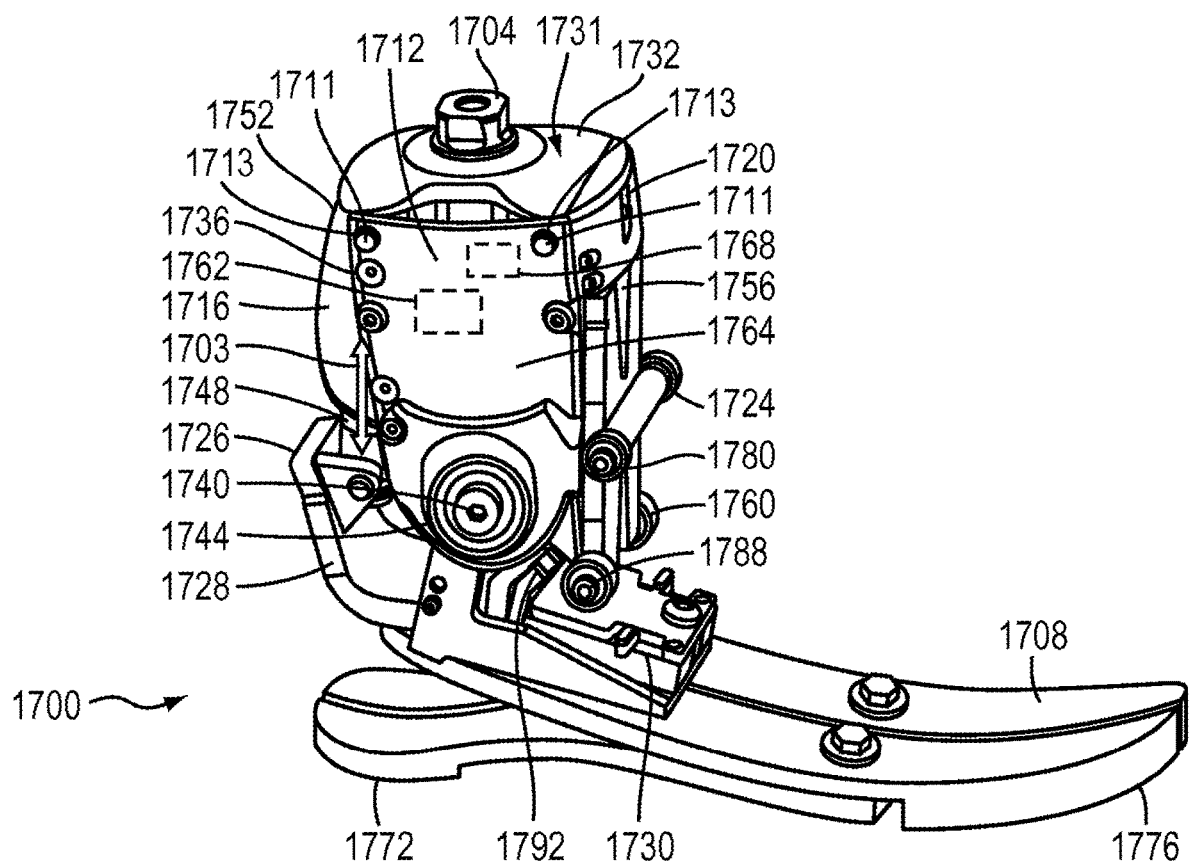
FIG. 5B depicts a mechanical configuration for the FIG. 5A embodiment.

FIG. 5B depicts a practical mechanical configuration for implementing the architecture shown in the FIG. 5A embodiment. In FIG. 5B, the torque sensor 1732 (which corresponds to ref. #66 in FIG. 5A) is positioned at the very top of the shank member 1716 (which corresponds to ref. #52 in FIG. 5A).

Another approach for determining the ankle torque $\Gamma_A$ is to break that torque up into its constituent components, and analyze the torque of each of those components separately. For example, in the design depicted in FIG. 6A-C, there are two components that contribute to the total torque: the torque applied by the series elastic element ($\Gamma_S$) and the torque applied by the bumper ($\Gamma_B$). The bumper is positioned between the shank portion of the ankle and the foot portion, and can also be considered a hardstop when the stiffness is high. In alternative embodiments, a spring may be used instead of a bumper. Note that the $\Gamma_B$ component only comes into play during bumper engagement (i.e., during dorsiflexion, when the shank member presses against a bumper that is affixed to the foot member, or, in alternative embodiments, when the foot member engages a bumper that is affixed to the shank member).

If each of the contributing components is known, the total ankle torque can be determined by vector-adding $\Gamma_S$ and $\Gamma_B$ (i.e., $\Gamma_A = \Gamma_S + \Gamma_B$). In the design depicted in FIG. 6B, both $\Gamma_S$ and $\Gamma_B$ can be determined as a function of displacement as measured by position sensors that are distributed throughout the design, like a motor encoder that detects the position of the motor and an ankle angle encoder that detects the angle of the ankle pivot.

Figure 6A:
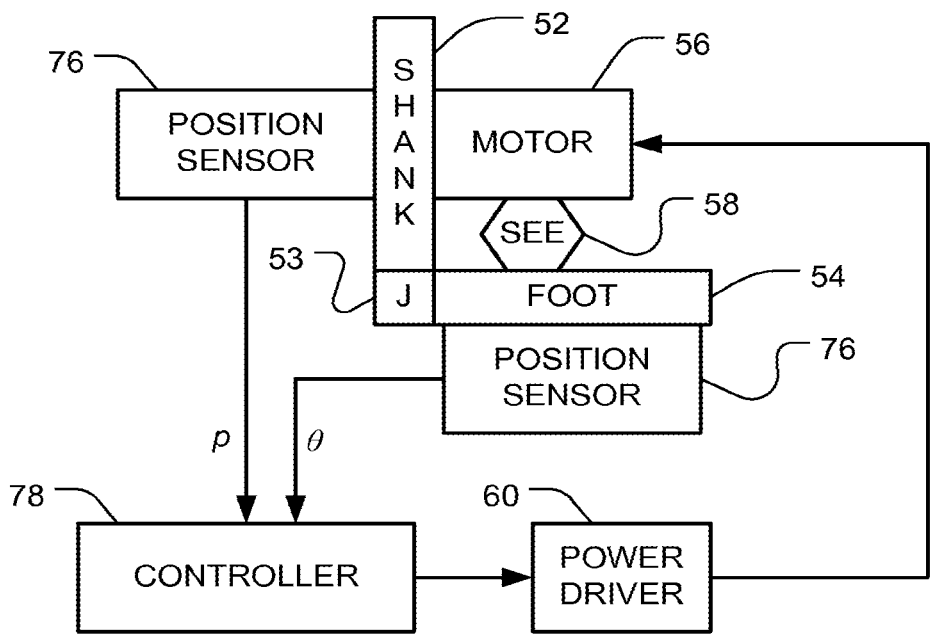
FIG. 6A is a block diagram of an embodiment that relies on deflections and torque vs. deflection characteristics.

We begin with $\Gamma_S$. In FIG. 6C, the motor 1B-102 drives a ballscrew 1B-106, and a digital encoder 1B-104 mounted on the motor measures the ballscrew extension p. If the foot were to be operated unloaded (e.g., when it is up in the air), for every given value of ballscrew extension p, the ankle joint 1B-108 would move to an angle $\beta(p)$. The $\beta(p)$ function can be determined empirically by lifting the device in the air so that it is unloaded, then driving the motor through its entire operating range, and measuring the resulting angle of the ankle joint 1B-108 at each value of p. Alternatively, $\beta(p)$ could be calculated based on the known geometry of the device. The $\beta(p)$ function is stored in a memory that is accessible by the controller 78 (shown in FIG. 6A) in any suitable format (e.g., as an equation or a lookup table).

During normal operation, the device will be loaded, and the actual angle θ of the ankle joint 1B-108 can be determined (e.g., by a high-resolution encoder, not shown, mounted on the ankle joint). In addition, the actual ballscrew extension p can be determined based on the output of the digital encoder 1B-104. The controller inputs p from the motor encoder and retrieves the unloaded angular position $\beta(p)$ from memory. It then inputs the actual angle θ from the ankle joint angle encoder and subtracts $\beta(p)$ from θ (i.e., the controller computes $\theta - \beta(p)$). That difference is the angular deflection of the SEE 1B-110. In some embodiments, a "single-turn" motor controller can be used. At power on, its absolute position within one motor turn and the absolute joint position can be used together to determine the absolute displacement of the ballscrew in relation to the end-of-travel in the plantarflexion direction.

After the deflection has been determined, the torque $\Gamma_S$ can be found because torque is a function of the deflection. In a simple model, the torque vs. deflection characteristics can be modeled as a linear function (Hooke's Law), so that $\Gamma_S = k_S \times \text{deflection}$, where $k_S$ is the spring rate for the SEE.

Figure 6B:
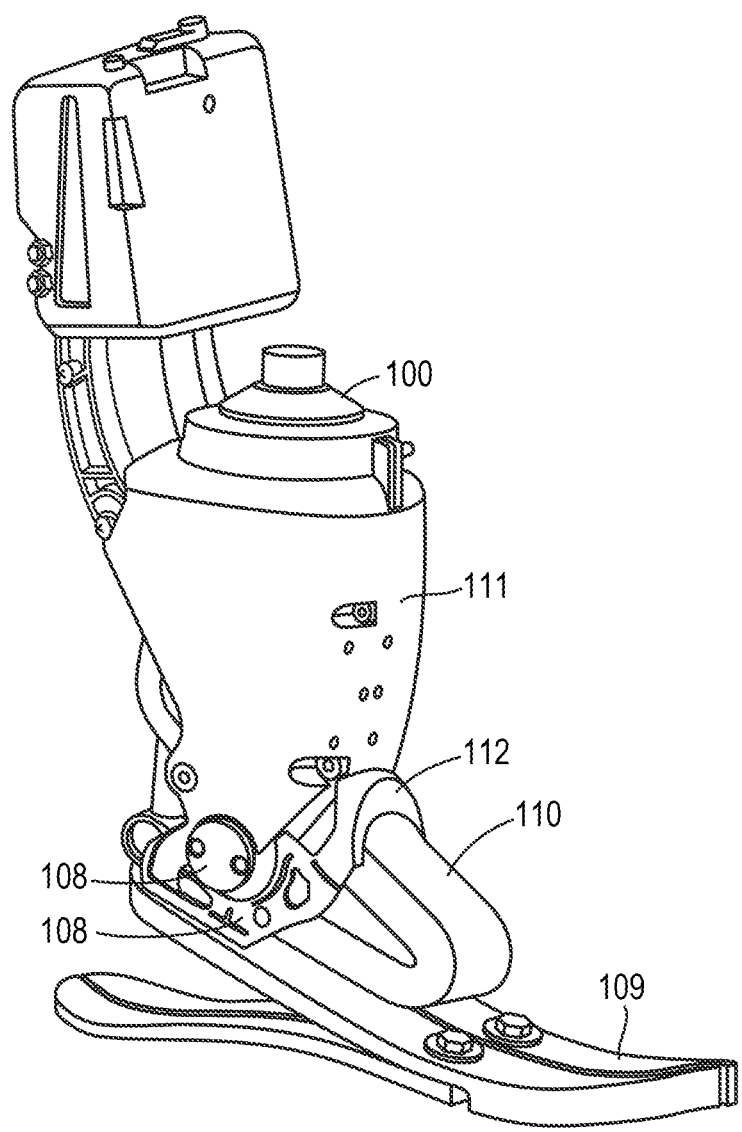
FIG. 6B depicts mechanical configuration for the FIG. 6A embodiment.
Figure 6C:
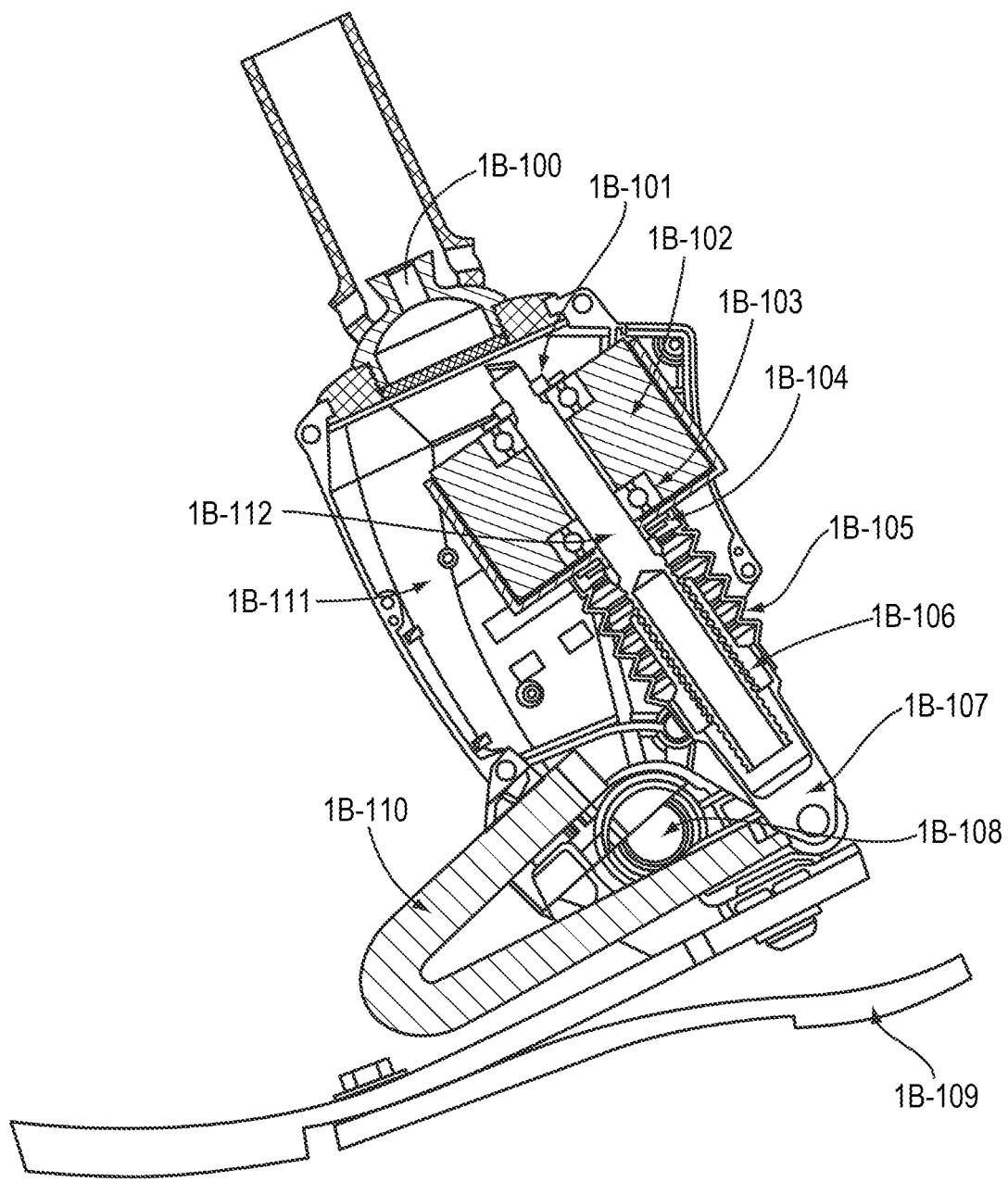
FIG. 6C depicts a section view of the FIG. 6B configuration.
Figure 9:
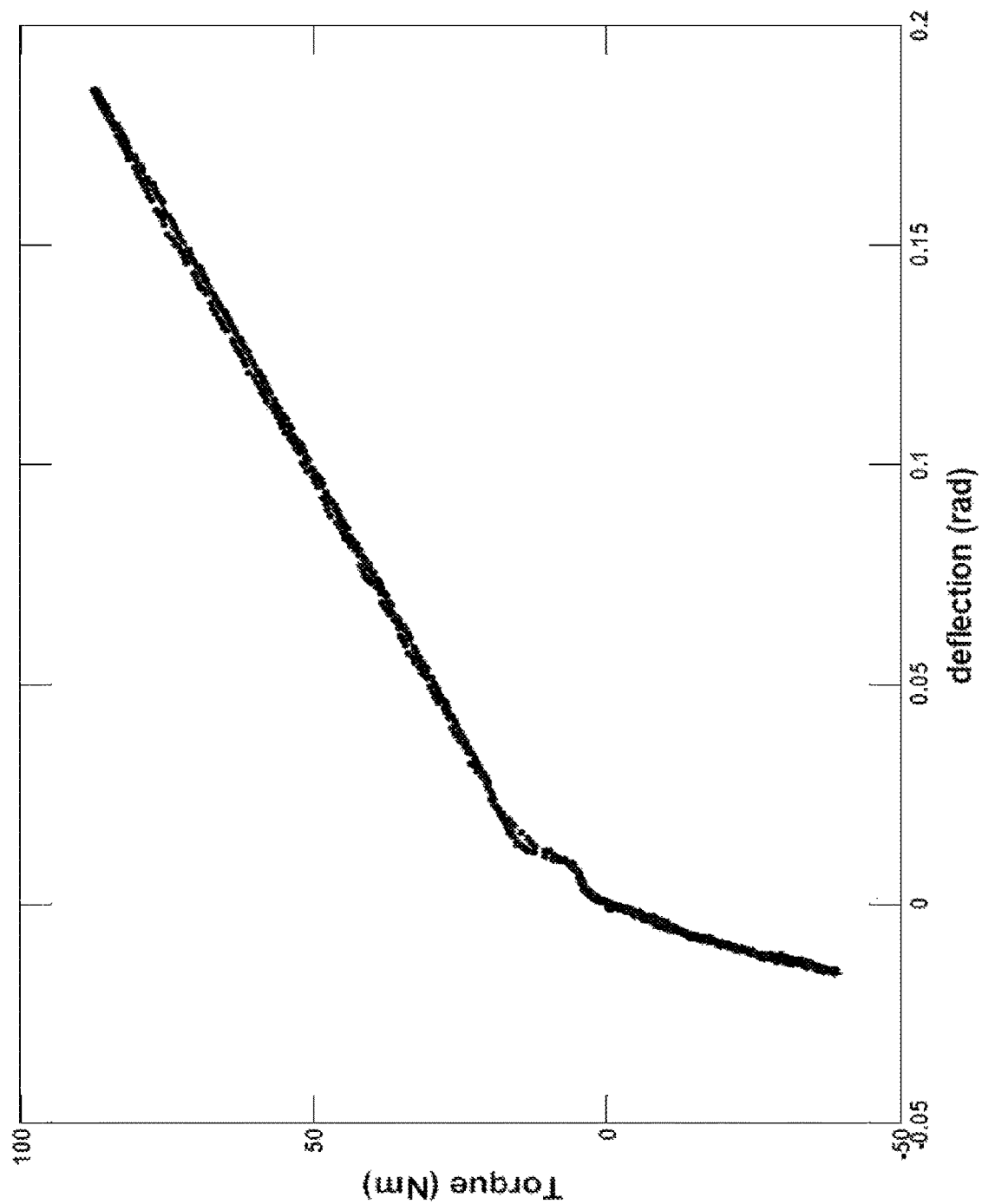
FIG. 9 depicts the torque vs. deflection characteristics for a series elastic element.

FIG. 9 depicts the torque vs. deflection characteristics for the series elastic element 1B-110 (shown in FIG. 6B). From these characteristics, a measured deflection can be used to determine $\Gamma_S$. Note that relying on an equation involving a spring constant $k_S$ is just one of many possible ways to determine the torque from a deflection, and alternative models and approaches for determining the torque vs. deflection characteristics may also be used (e.g., a lookup table, polynomial curve fitting, or non-linear estimation).

We turn next to the $\Gamma_B$ component. During dorsiflexion, the shank member 1B-111 pushes towards the foot member 1B-114, and a bumper 1B-112 that sits between those two members (and could be affixed to either member) is compressed. During testing of the previous generation designs, which used a relatively soft plastic for the bumper 1B-112, the inventors recognized that there is observable compliance in the bumper during engagement, in the range of 0.25° of deflection per 85 Nm peak reference load for a 250 lb amputee. When harder plastics are used (e.g., EPDM, with a 95 A durometer), there is much less deflection (e.g., 0.1° of deflection per 85 Nm peak reference load for a 250 lb amputee), and the force-deflection characteristic of this compliance became more stable and more easily modeled. Note that the metal shells that house the ankle mechanism will also flex measurably, and so can the foot structure and the member that contacts the bumper. When the flexural displacements are measured empirically for a particular design or sample of a design (e.g., using a test fixture), all of those flexures would be automatically accounted for.

Figure 7:
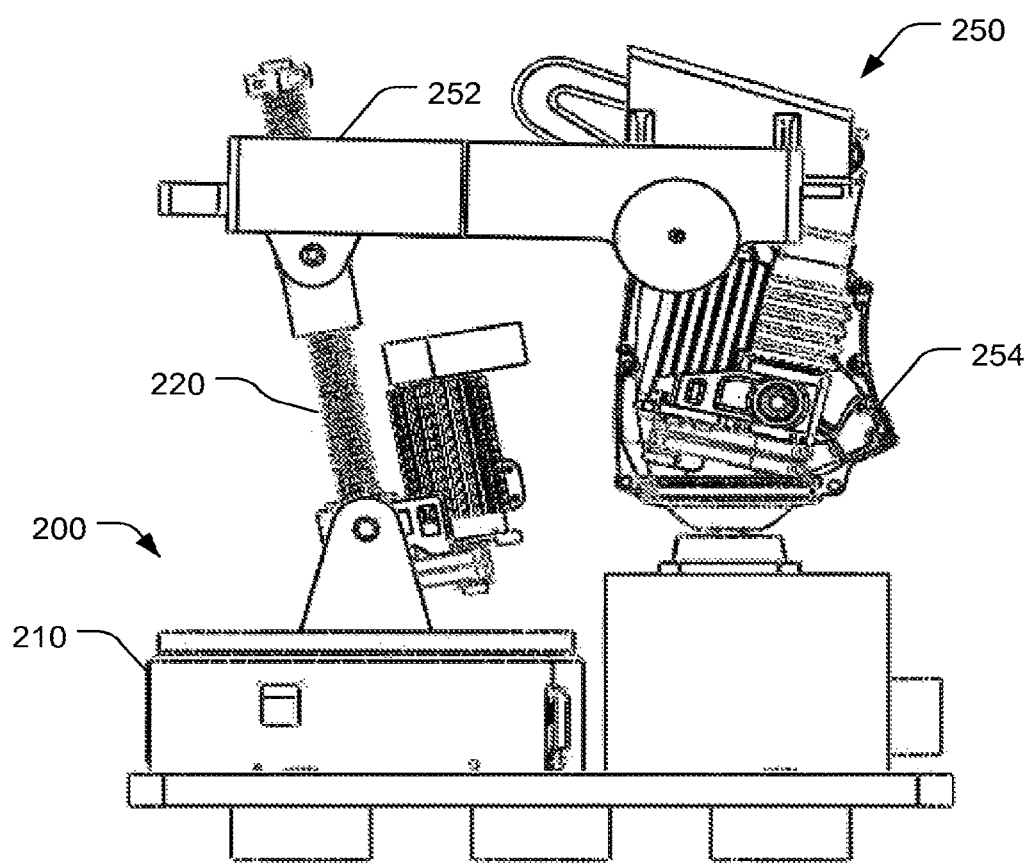
FIG. 7 depicts a test fixture for measuring torque vs. deflection characteristics.

The variation of $\Gamma_B$ with the compression of the bumper can be determined empirically for a given design or a particular instantiation of a design. One way to do this is to bolt a sample ankle/foot 250 into a test fixture 200, like the one shown in FIG. 7. The test fixture 200 preferably uses a six degree-of-freedom force-torque sensor 210 that simultaneously measures force and torque along and about three orthogonal axes (e.g., made by JR3, Inc.), with a backdrive ballscrew actuator 220 installed between the foot portion 252 of the ankle/foot 250 and the JR3 210. In this test fixture 200, the ankle/foot 250 is driven until the foot portion 252 makes initial contact with the bumper (shown in FIG. 6B) on the shank portion 254 of the ankle/font 250. The angle of initial contact is defined as $\theta_1$. Then, using the backdrive ballscrew actuator 220, the foot portion 252 is further driven to an angle $\theta_C$. The angle $\theta_C$ can be measured by the ankle encoder 1B-108 on the ankle/foot prosthesis (shown in FIG. 6C). As $\theta_C$ increases, the compression of the bumper increases, and the forces as determined by the JR3 210 are stored for every possible angle $\theta_C$.

Figure 8A:
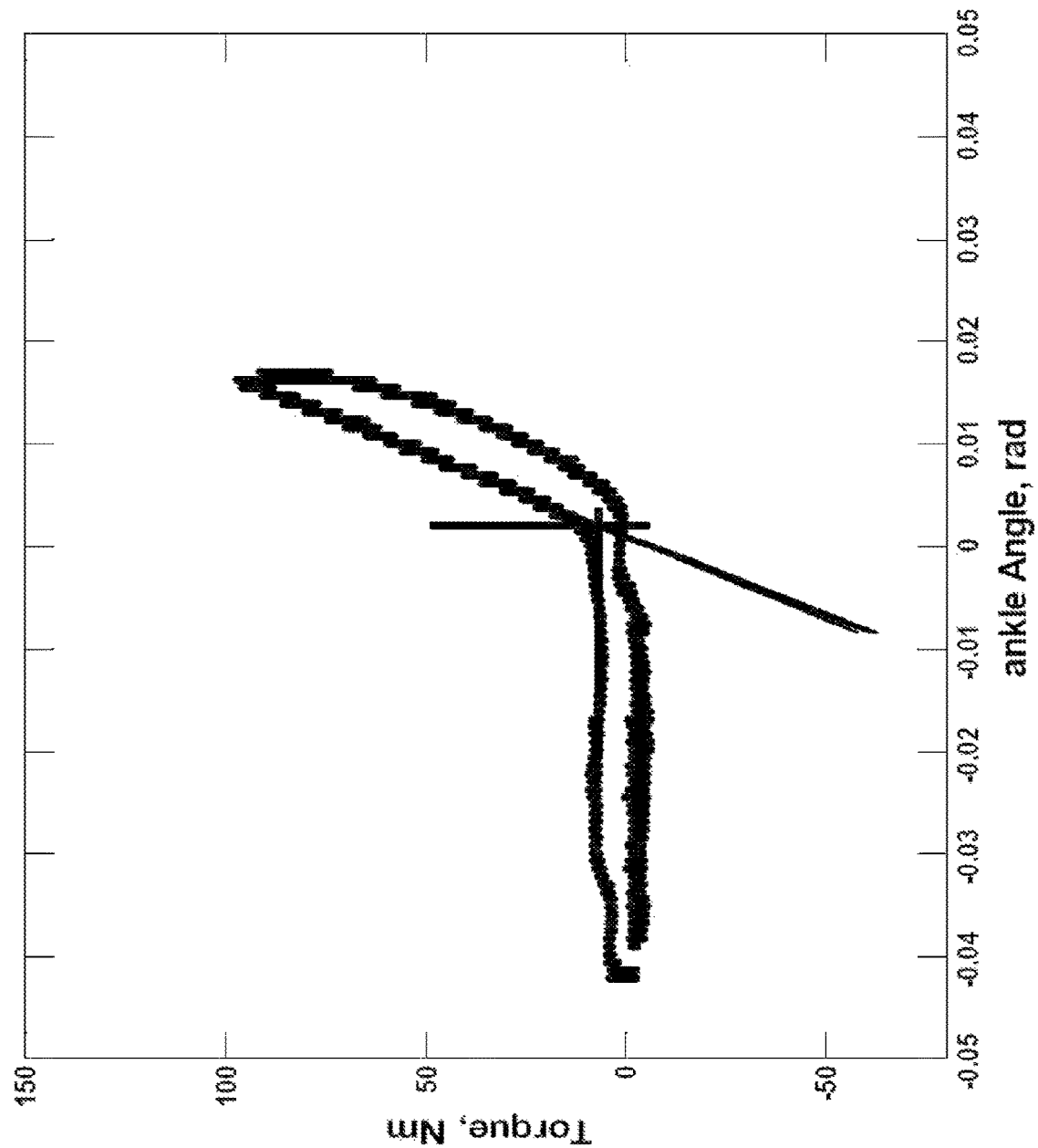
FIG. 8A is a graph from which a spring rate can be determined.

The Z (vertical) and Y (Horizontal) forces measured by the JR3 210 are summed using vector mathematics to determine the force along the backdrive screw axis. The ankle torque is then calculated by multiplying the axial force by the perpendicular moment arm, after subtracting any torque contribution from the SEE. The ankle torque versus ankle angle is plotted for a number of cycles (e.g., 10 cycles) for every possible angle $\theta_C$ and a least squares best fit line is calculated, assuming a linear relationship $\Gamma_B = K_S \times (\theta_C - \theta_S)$, where $K_S$ is the rotational spring rate for the bumper 1B-112. The slope of the resulting best-fit line is the spring rate $K_S$ of the bumper in Nm/rad as shown in FIG. 8A. In alternative embodiments, instead of using this linear relationship to model the bumper, alternative models and approaches for determining the torque vs. deflection characteristics in the design may also be used (e.g., a lookup table, polynomial curve fitting, or non-linear estimation).

Note that when increasing the torque (i.e., when the foot portion is being driven into the bumper and is compressing the bumper), the relationship of the ankle torque to ankle angle deflection is very linear. However when returning back to zero (decreasing torque), the curve is different. This discrepancy is due to the effect of the energy absorbing properties of the bumper. It is preferable to use the slope of the least squares best fit line for the increasing torque portion to determine the spring rate $K_S$ of the bumper.

Figure 8B:
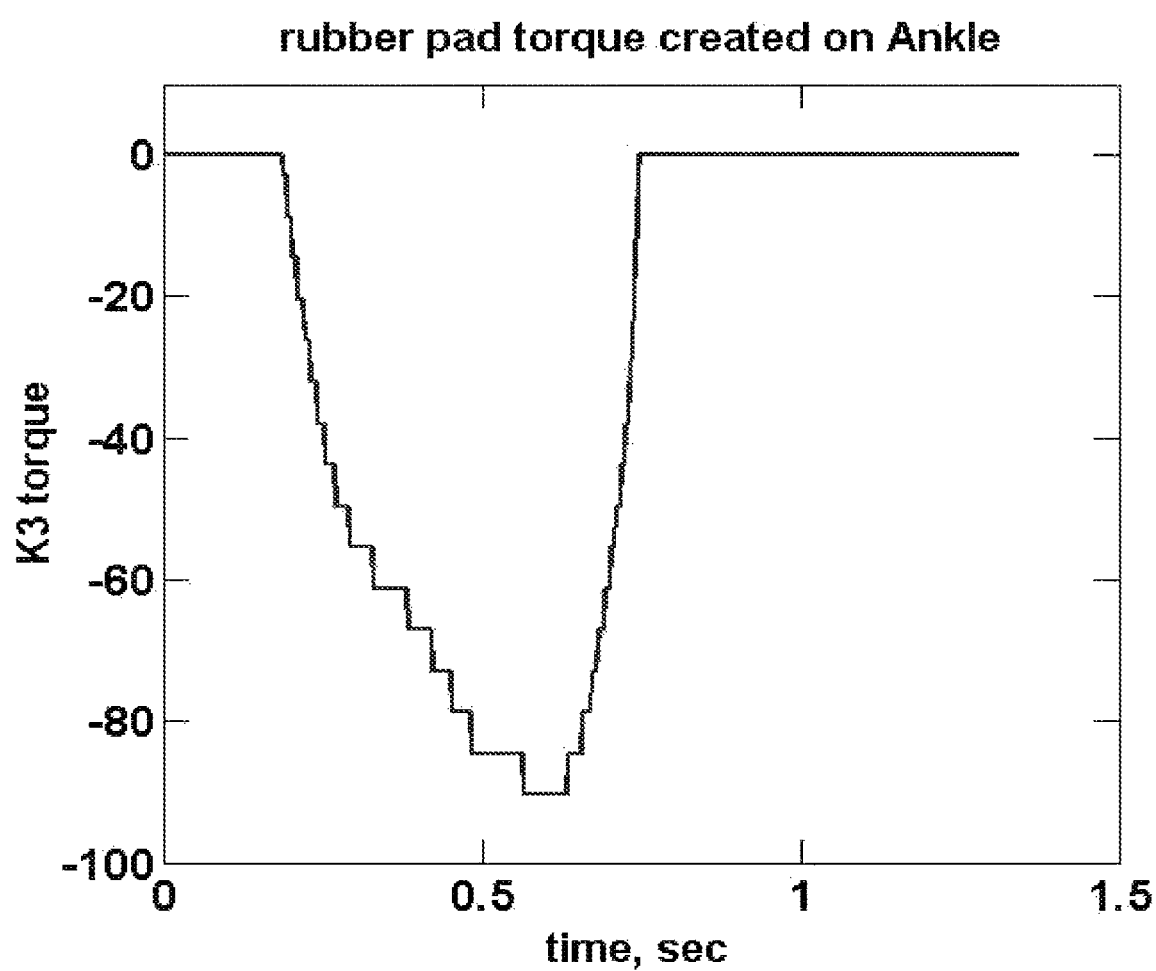
FIG. 8B is a graph depicting changes in a torque component over time.

FIG. 8B depicts the $\Gamma_B$ component of torque that is determined using this approach over time in a situation where the bumper is increasingly compressed for about half a second (until the torque reaches −90), and then released. The quantized nature of the $\Gamma_B$ torque is a function of the encoder resolution. This quantization can be minimized by utilizing higher resolution encoders. In one preferred embodiment, a 13 bit encoder (8196 counts/360 degrees) manufactured by Renishaw Inc (P/N RMB13BC1) is used. The Renishaw encoder employs a custom Hall-effect IC that measures the field angle arising from a single-pole, cylindrical magnet mounted on the foot structure in relation to the orientation of the IC affixed to a printed circuit assembly embedded in the ankle shell, Filtering of the angle measurement, using a FIR Low-Pass filter executing in a dedicated DSP, has been shown to extend the effective resolution to between 15-16 bits.

Once the torque vs. deflection characteristics of a bumper/ankle shell has been modeled (e.g., as explained above), the $\Gamma_B$ contribution at any given instant during operation of the prosthesis can be determined by measuring $\theta_C$ and plugging the result into the equation $\Gamma_B = K_S \times (\theta_C - \theta_L)$, or into an alternative model that models $\Gamma_B$ as a function of $\theta_C$. Thus, from a measured angular deflection $\theta_C$, the second torque component $\Gamma_B$ can be determined. In alternative embodiments, other ankle angle encoding means could be employed to determine how far the bumper has been compressed, including optical, magneto-restrictive and inductive sensors.

At this point, both the $\Gamma_S$ and $\Gamma_B$ components are known. $\Gamma_S$ can now be added to $\Gamma_B$ to arrive at $\Gamma_A$, and the resulting $\Gamma_A$ is used as an input to Equation 2 to control the motor.

FIG. 6A is a system block diagram for implementing this approach by determining $\Gamma_S$ and $\Gamma_B$ separately and then adding those components to arrive at $\Gamma_A$. Elements 52-60 are the same as the correspondingly numbered elements in FIG. 5A. Angular position sensors 76 measure the motor displacement p and the ankle joint displacement $\theta$, and send outputs representing those displacements to the controller 78. The controller 78 is programmed to convert those displacements to torque $\Gamma_S$ as explained above. In addition, the controller 78 is programmed to convert the ankle joint displacement $\theta$ to torque $\Gamma_B$ as explained above. The controller 78 then vector-adds $\Gamma_S$ to $\Gamma_B$ to determine $\Gamma_A$. The controller 78 then controls the motor 56 (with the assistance of the power driver 60, as in the FIG. 5A embodiment) by implementing Equation 2.

As mentioned above, n in Equation 2 can be tuned to make the device more comfortable for the user. Other parameters may also be similarly tuned, such as pff and the threshold angular rate $\omega_{TH}$, which affects the $Kv(\omega_x)$ function in Equation 2.

Referring now to FIG. 10, which is a $\Gamma-\Theta$ plot for the stance-phase, body-mass-normalized torque-angle, response of an intact ankle, additional parameters can be found that may be tuned in a prosthesis or orthosis to try to better mimic the intact ankle and thereby improve comfort and performance. Examples include, modulating impedance as the ankle-foot transitions from controlled plantar flexion (the slope of $K_{1-2}$), through controlled dorsiflexion (the slope of $K_{2-3}$), to powered plantarflexion (the slope of $K_{3-4}$. The initial values of these three impedances, and the initial value of 0 at toe-off ($\theta^*_{TOE-OFF}$) can be derived from the mean $\Gamma$–$\Theta$ response of intact ankles, and those initial values can then be tuned to suit the activity level, limb length, body-mass distribution and preferences of an individual user.

In the above-described embodiments, a single motor is used to implement both plantarflexion and dorsiflexion. But in alternative embodiments, that motor could be replaced by one motor for implementing plantarflexion, and another component for implementing dorsiflexion. In other alternative embodiments, a plurality of motors may be arranged in parallel to perform both plantarflexion and dorsiflexion. In still other embodiments, the electric motors described above can be replaced with other types of motors (e.g., hydraulic motors), in which case the controller and the power driver will have to be adjusted accordingly.

Note that while the concepts described above are explained in the context of prostheses, they can also be applied in the context of orthoses. In addition, while the embodiments described above all relate to ankles, the above-described concepts can be applied in other prosthetic and orthotic applications, such as hips, torso, and arms, in which case suitable modification should be made that will be appreciated by persons skilled in the relevant arts. For example, in the context of a knee, where the reflex occurs right during toe-off, the walking speed prediction would use "fresh" shank speed measurement just prior to toe-off. In those other contexts, the shank member can be generalized as a proximal member, the foot member can be generalized as a distal member, and dorsiflexion/plantarflexion can be generalized as varying the angle between the distal member and the proximal member. The above-described concepts can also be applied in the context of humanoid robots.

While the present invention has been disclosed with reference to certain embodiments, numerous modifications, alterations, and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

What is claimed is:

1. An ankle-foot prosthesis or orthosis apparatus comprising:
   a shank member;
   a foot member that is operatively configured with respect to the shank member so as to support walking and permit the foot member to plantarflex and dorsiflex with respect to the shank member;
   a motor configured to plantarflex the foot member with respect to the shank member;
   a series elastic element connected between at least one of (a) the motor and the shank member and (b) the motor and the foot member;
   a first sensor having an output serving as a surrogate for walking speed; and
   a controller configured to:
      determine, based on the output of the first sensor, a control value corresponding to at least one of: an angular rate $\omega_x$ of the shank member at a start of controlled dorsiflexion, an angular rate of a leg section above a knee of a user of the apparatus, a knee linear moving velocity in a stance phase, or a Cartesian trajectory of an ankle joint of the apparatus or the knee, and
      control the motor's torque, based on the determined control value, so that the motor's torque for slow walking speeds is lower than the motor's torque for fast walking speeds.

2. The apparatus of claim 1, wherein the motor is also configured to dorsiflex the foot member with respect to the shank member.

3. The apparatus of claim 1, wherein the first sensor comprises at least one of an angular rate sensor or an inertial measurement unit (IMU).

4. The apparatus of claim 1, wherein the controller is configured to (i) determine, based on the output of the first sensor, a control gain that varies with walking speed, wherein the control gain at slow walking speeds is lower than the control gain at fast walking speeds and (ii) determine a desired motor torque based on the control gain and a determined ankle torque, wherein controlling the motor's torque comprises driving the motor to achieve the desired motor torque.

5. The apparatus of claim 1, wherein the controller is configured to
   (i) determine, based on the output of the first sensor, the angular rate $\omega_x$ of the shank member,
   (ii) determine a control gain $Kv(\omega_x)$ that is a function of the angular rate, wherein the control gain at low angular velocities is lower than the control gain at high angular velocities, and
   (iii) determine a desired motor torque based on the equation Motor Torque=$Kv(\omega_x) \times pff \times (\text{normalized\_Torque})^n$, where pff is a constant and n is between 2 and 7, wherein controlling the motor's torque comprises driving the motor to achieve the desired motor torque.

6. The apparatus of claim 5, wherein $Kv(\omega_x)=0$ when $\omega_x=0$, $Kv(\omega_x)=1$ when $\omega_x$ exceeds a threshold $\omega_{TH}$, and $Kv(\omega_x)$ is a monotonically increasing function between $\omega_x=0$ and $\omega_{TH}$.

7. The apparatus of claim 6, wherein the motor is also configured to dorsiflex the foot member with respect to the shank member.

8. The apparatus of claim 1, further comprising a second sensor having an output from which ankle torque can be determined, and wherein the controller is configured to control the motor's torque based in part on the output of the second sensor.

9. The apparatus of claim 8, wherein the second sensor measures ankle torque directly.

10. The apparatus of claim 8, wherein the second sensor has a second sensor output from which a deflection of series elastic element can be determined, and the controller computes the torque based in part on the second sensor output.

11. The apparatus of claim 8, wherein the second sensor senses a position of the motor, the apparatus comprises a third sensor that senses an angle of the foot member with respect to the shank member, and the controller computes the torque based on the sensed position of the motor and the sensed angle.

12. The apparatus of claim 8, wherein the second sensor senses a position of the motor, the apparatus comprises a third sensor that senses an angle of the foot member with respect to the shank member, and the controller determines a torque component $\Gamma_S$ based on the sensed position of the motor, the sensed angle, and a torque vs. deflection characteristics of the series elastic element.

13. The apparatus of claim 12, further comprising a bumper that is compressed when the foot member is sufficiently dorsiflexed with respect to the shank member,
wherein the controller determines a torque component FB based on the sensed angle and a torque vs. deflection characteristics of the bumper, and
wherein the controller determines a total torque based on $\Gamma_s$ and $\Gamma_B$.

14. The apparatus of claim 1, wherein control of the torque of the motor is based on non-linear positive feedback according to the output of the first sensor.

15. The apparatus of claim 14, wherein the non-linear positive feedback involves adjustment of a parameter of a power control gain function, the parameter comprising at least one of a power control gain or a power exponent.

16. A method, comprising:
receiving a sensor output associated with an ankle-foot prosthesis or orthosis, the sensor output serving as a surrogate for a walking speed of a user of the prosthesis or orthosis;
determining, based on the sensor output, a control value corresponding to at least one of: (i) an angular rate w of a shank member at a start of controlled dorsiflexion, the shank member operatively connected to a foot member of the prosthesis or orthosis so as to support walking and permit the foot member to plantarflex and dorsiflex with respect to the shank member, (ii) an angular rate of a leg section above a knee of a user of the prosthesis or orthosis, (iii) a knee linear moving velocity in a stance phase, or (iv) a Cartesian trajectory of an ankle joint of the prosthesis or orthosis or the knee; and
transmit a torque control signal to a motor of the prosthesis or orthosis, the torque control signal being calculated based on the determined control value and configured to control the motor's torque so that the motor's torque for slow walking speeds is lower than the motor's torque for fast walking speeds.

17. The method of claim 16, wherein the determining comprises determining a control gain that varies with walking speed, wherein the control gain at slow walking speeds is lower than the control gain at fast walking speeds, and further comprising:
determining a desired motor torque based on the control gain and a determined ankle torque, wherein
the control signal is configured to drive the motor to achieve the desired motor torque.

18. The method of claim 16, further comprising:
(i) determining, based on the sensor output, the angular rate $\omega_x$ of the shank member,
(ii) determining a control gain $Kv(\omega_x)$ that is a function of the angular rate, wherein the control gain at low angular velocities is lower than the control gain at high angular velocities, and
(iii) determining a desired motor torque based on the equation Motor Torque=$Kv(\omega_x) \times pff \times (\text{normalized\_Torque})^n$, where pff is a constant and n is between 2 and 7, wherein the control signal is configured to drive the motor to achieve the desired motor torque.

19. The method of claim 18, wherein $Kv(\omega_x)=0$ when $\omega_x=0$, $Kv(\omega_x)=1$ when $\omega_x$ exceeds a threshold $\omega_{TH}$, and $Kv(\omega_x)$ is a monotonically increasing function between $\omega_x=0$ and $\omega_{TH}$.

* * * * *